(12) United States Patent
Blue et al.

(10) Patent No.: US 9,784,102 B2
(45) Date of Patent: Oct. 10, 2017

(54) VARIABLE GEOMETRY FRACTURE SEALING TESTER

(71) Applicant: M-I L.L.C., Houston, TX (US)

(72) Inventors: Aaron Blue, Houston, TX (US); John Moffitt, Sugar Land, TX (US)

(73) Assignee: M-I L.L.C., Houston, TX (US)

( * ) Notice: Subject to any disclaimer, the term of this patent is extended or adjusted under 35 U.S.C. 154(b) by 243 days.

(21) Appl. No.: 14/399,385

(22) PCT Filed: May 10, 2013

(86) PCT No.: PCT/US2013/040572
§ 371 (c)(1),
(2) Date: Nov. 6, 2014

(87) PCT Pub. No.: WO2013/170166
PCT Pub. Date: Nov. 14, 2013

(65) Prior Publication Data
US 2015/0135815 A1   May 21, 2015

Related U.S. Application Data

(60) Provisional application No. 61/645,359, filed on May 10, 2012.

(51) Int. Cl.
*E21B 49/08* (2006.01)
*G01N 15/08* (2006.01)
*G01N 33/28* (2006.01)

(52) U.S. Cl.
CPC ......... *E21B 49/08* (2013.01); *G01N 15/0806* (2013.01); *G01N 33/2823* (2013.01)

(58) Field of Classification Search
None
See application file for complete search history.

(56) References Cited

U.S. PATENT DOCUMENTS

| | | | |
|---|---|---|---|
| 3,286,510 A * | 11/1966 | Parker | G01N 33/00 210/321.87 |
| 4,748,849 A | 6/1988 | Jamison et al. | |
| 6,055,874 A * | 5/2000 | Onan | E21B 49/00 73/865.6 |
| 6,543,276 B2 * | 4/2003 | Murphy, Jr. | G01N 15/08 73/152.25 |
| 7,900,504 B2 | 3/2011 | Huynh et al. | |
| 8,312,920 B2 * | 11/2012 | Tehrani | G01N 1/34 166/267 |

(Continued)

OTHER PUBLICATIONS

International Search Report and Written Opinion of PCT Application Serial No. PCT/US2013/040572 dated Aug. 19, 2013 (14 pages).

*Primary Examiner* — Jill Culler
(74) *Attorney, Agent, or Firm* — Sara K. M. Hinkley

(57) ABSTRACT

A fracture insert is disclosed including a first cylindrical portion and a second cylindrical portion disposed opposite the first cylindrical portion defining a radial gap therebetween to form an axial flow channel. The axial flow channel provides a flow path for a drilling fluid from a top of the cylindrical portions to a bottom of the cylindrical portions and the radial gap provides a flow path for the drilling fluid from the axial flow channel to a radial terminus of the first cylindrical portion and the second cylindrical portion.

25 Claims, 11 Drawing Sheets

(56) References Cited

U.S. PATENT DOCUMENTS

| | | |
|---|---|---|
| 8,448,500 B2 | 5/2013 | Huynh et al. |
| 8,573,048 B2 | 11/2013 | Slater et al. |
| 2011/0185795 A1 | 8/2011 | Colquhoun |
| 2011/0295509 A1 | 12/2011 | Huynh et al. |

* cited by examiner

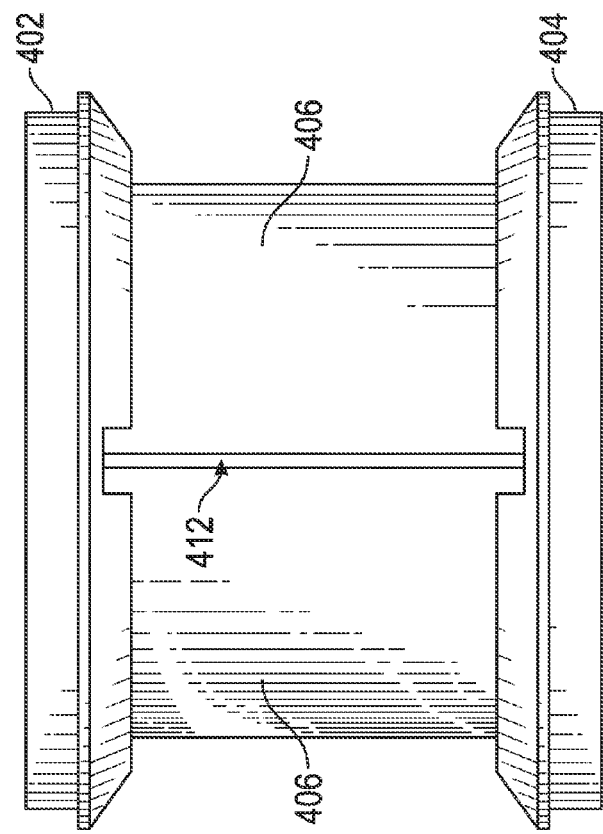
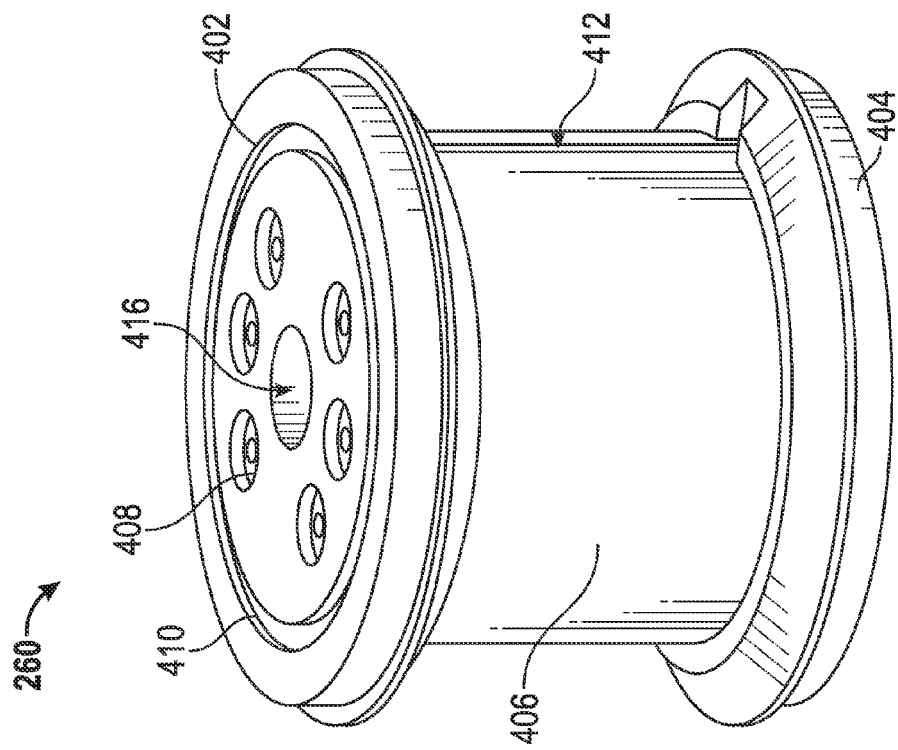
FIG. 4B
FIG. 4A

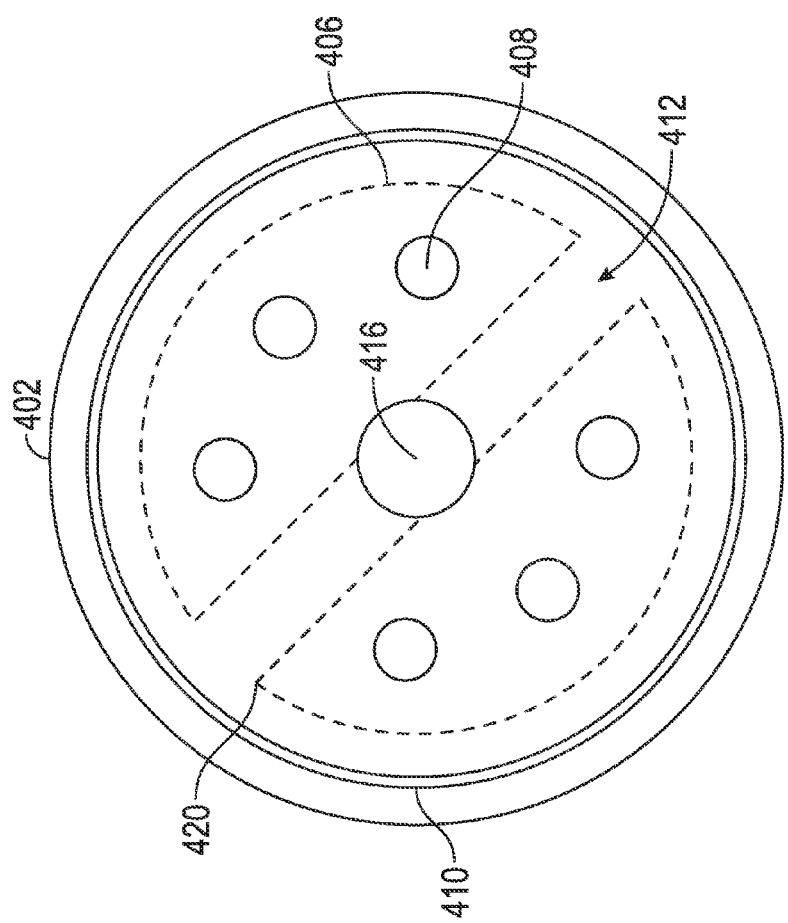
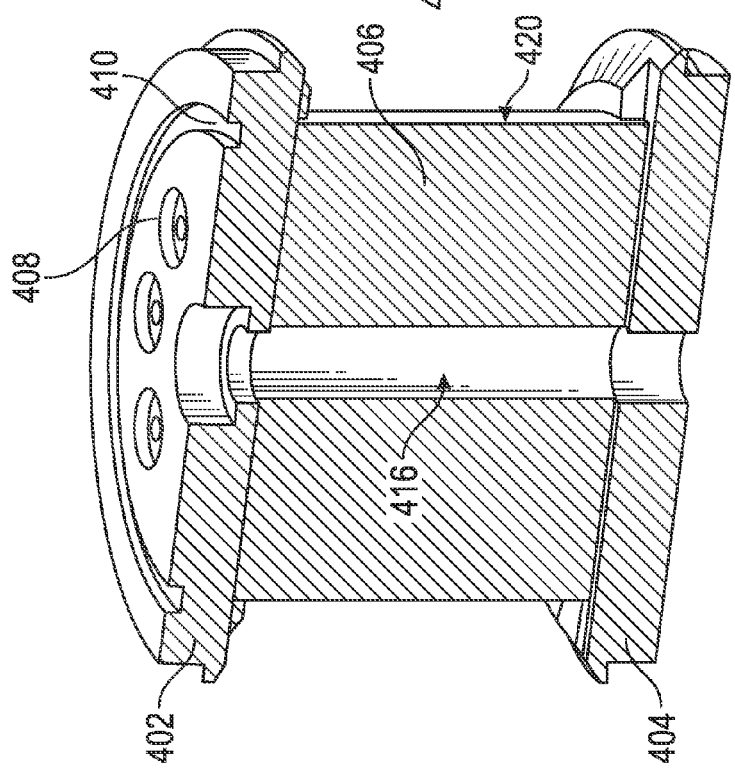
FIG. 4D
FIG. 4C

VARIABLE GEOMETRY FRACTURE SEALING TESTER

BACKGROUND

The present disclosure generally relates to systems and methods for testing drilling fluids for drilling operations. More particularly, the present disclosure relates to methods and systems for determining sealing characteristics and properties of fluid loss control materials and optimizing drilling fluids using such materials.

During the drilling of a wellbore, various fluids are often used in the well for a variety of functions. The fluids may be circulated through a drill pipe and drill bit into the wellbore, and then may subsequently flow upward through the wellbore to the surface. During this circulation, the drilling fluid may act to remove drill cuttings from the bottom of the hole to the surface, to suspend cuttings and weighting material when circulation is interrupted, to control subsurface pressures, to maintain the integrity of the wellbore until the well section is cased and cemented, to isolate the fluids from the formation by providing sufficient hydrostatic pressure to prevent the ingress of formation fluids into the wellbore, to cool and lubricate the drill string and bit, and/or to maximize penetration rate.

In most drilling procedures the drilling fluid takes the form of a "mud," i.e., a liquid having solids suspended therein. The solids function to impart desired rheological properties to the drilling fluid and also to increase the density thereof in order to provide a suitable hydrostatic pressure at the bottom of the well. The drilling mud may be either a water-based or an oil-based mud.

Drilling muds may consist of polymers, biopolymers, clays, and organic colloids added to a water-based fluid to obtain the required viscosity and filtration properties. Heavy minerals, such as barite or calcium carbonate, may be added to increase density. Solids from the formation are incorporated into the mud and often become dispersed in the mud as a consequence of drilling. Further, drilling muds may contain one or more natural and/or synthetic polymeric additives, including polymeric additives that increase the rheological properties (e.g., plastic viscosity, yield point value, gel strength) of the drilling mud, and polymeric thinners and flocculents.

Polymeric additives included in the drilling fluid may act as fluid loss control agents. Fluid loss control agents, such as starch, prevent the loss of fluid to the surrounding formation by reducing the permeability of filter cakes formed on the newly exposed rock surface. In addition, polymeric additives are employed to impart sufficient carrying capacity and thixotropy to the mud to enable the mud to transport the cuttings to the surface and to prevent the cuttings from settling out of the mud when circulation is interrupted.

As such, many drilling fluids may be designed to form a thin, low-permeability filter cake to seal permeable formations penetrated by the drill bit. The filter cake is essential to prevent or reduce both the loss of fluids into the formation and the influx of fluids present in the formation. Upon completion of drilling, the filter cake may stabilize the wellbore during subsequent completion operations such as placement of a gravel pack in the wellbore. Filter cakes often comprise bridging particles, cuttings created by the drilling process, polymeric additives, and precipitates. One feature of a drilling fluid is to retain these solid and semi-solid particles as a stable suspension, free of significant settling over the time scale of drilling operations.

Once the drilling fluid is lost into the formation, it becomes difficult to remove. Calcium and zinc-bromide brines can form highly stable, acid insoluble compounds when reacted with the formation or substances contained therein. This reaction may reduce the permeability of the formation to any subsequent out-flow of the targeted hydrocarbons. The most effective way to prevent such damage to the formation is to limit fluid loss into the formation.

Thus, providing effective fluid loss control is highly desirable to prevent damaging the formation in, for example, completion, drilling, drill-in, displacement, hydraulic fracturing, work-over, packer fluid emplacement or maintenance, well treating, or testing operations. In certain drilling environments, the formation may be exceptionally prone to damage from fluid loss. Examples of such drilling operations may include depleted zone drilling.

Depleted drilling zones may be especially prone to fractures (i.e., cracks and disruptions in a formation that may be either naturally formed or induced). Fracturing during the drilling operation, also known as induced fracturing, often occurs in permeable rocks such as sandstone and carbonates or within impermeable rock typified by shale formations. Induced fracturing is of particular concern when drilling into depleted zones where a drop in pore pressure is anticipated as the reserves decline. In these situations, drilling then becomes more of a technical challenge as the mud weight required to support a section may exceed the tensile strength, or fracture resistance, of the formation. This in turn could lead to increased drilling fluid losses and increased well costs.

In order to prevent fluid loss and increased well costs, it is desirable to develop methods and systems of testing and optimizing drilling fluids and/or fluid loss control materials for drilling in permeable and impermeable formations.

SUMMARY

In one aspect, embodiments disclosed herein relate to a fracture insert. The fracture insert may include a first cylindrical portion and a second cylindrical portion disposed opposite the first cylindrical portion defining a radial gap therebetween to form an axial flow channel. The axial flow channel provides a flow path for a drilling fluid from a top of the cylindrical portions to a bottom of the cylindrical portions and the radial gap provides a flow path for the drilling fluid from the axial flow channel to a radial terminus of the first cylindrical portion and the second cylindrical portion.

In another aspect, embodiments disclosed herein relate to a vessel. The vessel may include an inlet for receiving a drilling fluid, a filtrate outlet, a fluid outlet, and a fracture insert disposed within the vessel. The insert may include a first cylindrical portion opposite a second cylindrical portion defining a radial gap therebetween and forming an axial flow channel. The axial flow channel may provide a flow path for the drilling fluid from the inlet to the outlet and the radial gap may provide a flow path for the drilling fluid from the inlet to the outlet.

In another aspect, embodiments disclosed herein relate to a system. The system may include a vessel with an inlet for receiving a drilling fluid, a filtrate outlet, a fluid outlet, and a fracture insert disposed within the vessel. The insert may include a first cylindrical portion opposite a second cylindrical portion defining a radial gap therebetween and forming an axial flow channel. The axial flow channel may provide a flow path from the inlet to the fluid outlet and the radial gap may provide a flow path from the inlet to the filtrate outlet. The system may include at least one of a base fluid container in fluid communication with the inlet, a test fluid container in fluid communication with the inlet, a filtrate container in fluid communication with the filtrate outlet, and a collection container in fluid communication with the fluid outlet.

In another aspect, embodiments disclosed herein relate to a method including the step of injecting a first test fluid having a fluid loss control material to a vessel. The vessel may include an inlet, a filtrate outlet, a fluid outlet, and a fracture insert disposed within the vessel. The insert may include a first cylindrical portion opposite a second cylindrical portion defining a radial gap therebetween and forming an axial flow channel. The axial flow channel may provide a flow path from the inlet to the fluid outlet and the radial gap may provide a flow path from the inlet to the filtrate outlet. The method further includes measuring a fluid loss through the radial gap.

In yet another aspect, embodiments disclosed herein relate to a method including the steps of injecting a drilling fluid having a first fluid loss control material particle size into a vessel, measuring a fluid loss through the radial gap, determining a sealing parameter based on the fluid loss, and adjusting the fluid loss control material particle size based on the sealing parameter. The vessel of the method may include an inlet, a filtrate outlet, a fluid outlet, and a fracture insert disposed within the vessel. The insert may include a first cylindrical portion opposite a second cylindrical portion defining a radial gap therebetween and forming an axial flow channel, the axial flow channel providing a flow path from the fluid inlet to the fluid outlet, and the radial gap providing a flow path from the fluid inlet to the filtrate outlet.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF DRAWINGS

FIGS. 4A-4D show various views of a fracture insert according to embodiments of the present disclosure.

DETAILED DESCRIPTION

Figure 1:
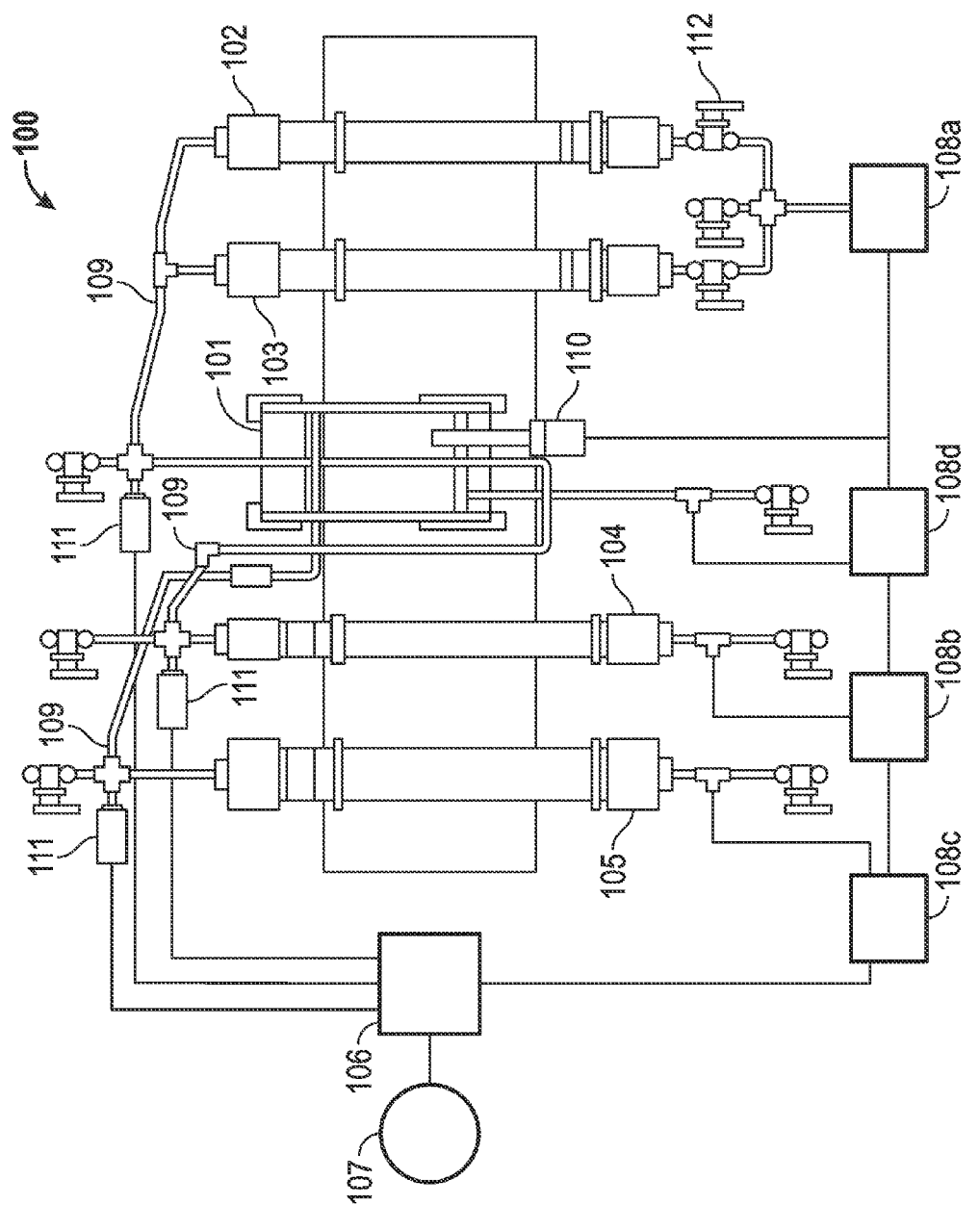
FIG. 1 shows a system for testing a drilling fluid in accordance with embodiments of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, components, and/or groups, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element is referred to as being "on," "engaged to," "connected to," or "coupled to" another element or layer, it may be directly on, engaged, connected or coupled to the other element or layer, or intervening elements or layers may be present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The present disclosure generally relates to systems and methods for testing drilling fluids for drilling operations. More particularly, the present disclosure relates to methods and systems for determining sealing characteristics and properties of fluid loss control materials and optimizing drilling fluids using such materials.

Embodiments described herein include a testing system for determining the sealing characteristics of drilling fluids, including both oil- and water-based fluids, as may be used in drilling earth formations. The types of formations discussed below generally include impermeable formations such as shale, however, the present disclosure may also find use when testing drilling fluids used while drilling permeable formations such as sandstone and carbonates. Those of ordinary skill in the art will appreciate that the type of formation being tested and the specific fluids discussed below are not a limitation on the scope of the present disclosure. As such, all discussed examples are merely exemplary, and the systems of testing and methods of determining sealing characteristics and optimizing drilling fluids are exemplary as well.

Referring to FIG. 1, a system 100 for testing a drilling fluid in accordance with embodiments of the present disclosure is shown. In this embodiment, system 100 may include a vessel 101 and several fluid containers 102, 103, 104, and 105. System 100 may also include a data acquisition system 106, an information processor 107, and a series of pumps 108*a-d*. In another aspect, the data acquisition system 106 and/or the information processor 107 may be in communication with the system 100.

As used herein, an information processor may include any instrumentality or aggregate of instrumentalities operable to receive, compute, process, originate, transmit, classify, retrieve, store, display, record, reproduce, handle, or utilize any form of information, intelligence, or data for business, scientific, or other purpose. For example, an information processor may be a computer, electronic device, display, network server, storage device, and/or other suitable device.

More specifically, system 100 may include a base fluid container 102 and a test fluid container 103 in fluid communication with vessel 101. Containers 102 and 103 may include any type of containers used to contain drilling fluid, and as such, may include plastic, steel, or composite containers. Those of ordinary skill in the art will appreciate that because the system is pressurized, the containers may need to be able to handle the requisite pressure requirements of system 100. Likewise, the fluid connections providing fluid communication between containers 102 and 103 and vessel 101 may also need to able to handle the pressure requirements of the system, and as such, appropriate fluid lines 109 may include steel lines, reinforced plastic lines, and other lines as known to those of ordinary skill in the art.

In this embodiment, a first pump 108a may be used to pressurize system 100 by providing a pressure to base fluid container 102 and test fluid container 103. A base fluid may be stored in base fluid container 102, and a test fluid may be stored in test fluid container 103. Pump 108a may be used to deliver both the base fluid and the test fluid, as required by the testing operation, to vessel 101. In one aspect, pump 108a may include a syringe pump, however, those of ordinary skill in the art will appreciate that other types of pumps may be used to inject a fluid from containers 102 and 103 to vessel 101.

A flow through container 104 may be used to collect a flow through fluid from vessel 101 during the testing. Similar to containers 102, and 103, flow through container 104 may also include any type of container used to hold drilling fluids, and as such, may include steel or plastic containers. Flow through container 104 is also fluidly coupled to vessel 101 via fluid lines 109, as described with respect to containers 102 and 103 above. In this embodiment, a second pump 108b provides a back pressure to the matrix (not shown) of vessel 101. This pump may also be used to record the volume of filtrate lost through the matrix as accumulated in flow through container 104. In one aspect, second pump 108b may include a syringe pump, however, other pumps may be used that create a back pressure, as described above.

A collection container 105 may be used to collect a fluid from vessel 101 during the testing. Collection container 105 may also include any type of container used to hold drilling fluids, and as such, may include steel or plastic containers. Collection container 105 may be in fluid communication with vessel 101 via fluid lines 109, as described with respect to containers 102, 103, and 104 above. In this embodiment, a third pump 108c provides a back pressure to vessel 101. This pump may also be used to record the volume of fluid lost through the fracture as accumulated in filtrate container 104. In one aspect, third pump 108c may include a syringe pump, however, other pumps may be used that create a back pressure, as described above.

Vessel 101 may include interchangeable internals, as will be described below, providing for flexibility in testing. When needed, a fourth pump 108d may be coupled to vessel 101 for various purposes, such as to control a constant fracture width of media plates (not shown) disposed in vessel 101, as described in U.S. Pat. No. 7,900,504, for example. Fourth pump 108d may be controlled, in this embodiment, by a linear transducer 110 that may be operatively coupled to vessel 101 and fourth pump 108d to maintain a constant fracture wide of media plates (not shown) based on a reading of linear distance between the media plates. Said another way, linear transducer 110 may be used to control the fracture closure pressures. Those of ordinary skill in the art will appreciate that in other embodiments, linear transducer 110 may not be required, and the fracture closure pressures may be recorded by other types of transducers, pressure gauges, or other devices as known to those of skill in the art. In one aspect, third pump 108d may include a syringe pump, however, other pumps may be used that provide a pressure to vessel 101 and/or transducer 110 to control and/or measure a pressure inside vessel 101.

Those of ordinary skill in art will appreciate that in other systems, a single pump or other configurations of pumps may provide the requisite pressures to test a drilling fluid. As such, the precise configuration of pumps 108 described in FIG. 1 is not a limitation on the scope of the present disclosure.

System 100 may also include a plurality of sensors 111 that may be used to measure, inter alia, pressures, temperatures, densities, conductivities, flow rates, flow levels, or other parameters of system 100 or of drilling fluids being tested. Thus, sensors 111 may be used to collect data or to determine a condition of system 100. In this embodiment, sensors 111 are operatively coupled to data acquisition system 106. Data acquisition system 106 may include any device used to sense, collect, handle, process, document, or analyze data from system 100. Examples of data acquisition systems 106 that may be used in aspects of the present disclosure include analog-to-digital converters and digital-to-analog converters. Thus, in certain embodiments, data acquisition system 106 may receive a digital and/or analog input/output from sensors 111, pumps 108a-d, or directly from another component of system 100, collect and/or analyze the data, and in certain embodiments, transfer the data to an information processor 107 for further analyzing. Examples of methods of transferring the data from data acquisition system 106 to information processor 107 may include, for example, via a USB (universal serial bus), parallel ports, serial communication ports, direct data acquisition plug-in boards, or remote terminal connections. Thus, in certain embodiments, data acquisition system 106 may be directly or indirectly configured to transfer data to information processor 107.

Likewise, information processor 107 may be used to send instructions to data acquisition system 106, sensors 111, pumps 108a-d, or other components of system 100. Examples of such instructions may include instructions to control an operational parameter, such as, a pressure, a flow rate of a fluid, a distance between media plates, or instructions to request additional data from a component of system 100. Such instructions may be sent from information processor 107 either through data acquisition system 106 or, in certain embodiments, directly to an individual component of system 100. Those of ordinary skill in the art will appreciate that information processor 107 may be used to collect data, analyze data, and/or to control the testing.

Additionally, information processor 107 may be used to render visual representations of collected and analyzed data. Visual representations may include the generation of data tables, numerical representations, graphical representations, or other forms of displaying data. Examples of such visual representations will be discussed in greater detail below.

Other components of system 100 may include a plurality of valves 112, which may be controlled via data acquisition system 106, information processor 107, or otherwise manually actuated to control an operational parameter of system 100. Those of ordinary skill in the art will appreciate that any number of valves, valve types, and location of such valves will vary according to the design of system 100. However, generally, it may be beneficial to have valves in locations to control both the flow of fluids through system 100 and the pressure of portions of system 100. Furthermore, those of ordinary skill in the art will appreciate that other design variations to system 100 may be possible that include additional components such as, for example, multiple information processors 107, data acquisition systems 106, multiple test vessels 101, additional fluid containers 102, 103, 104, and 105, or additional sensors 111 including other measuring devices.

While system 100 has been discussed generally above, the construction and components parts of vessel 101 will be discussed in detail below so that the operation and testing conditions system 100 provides for is more clearly understood.

Figure 2:
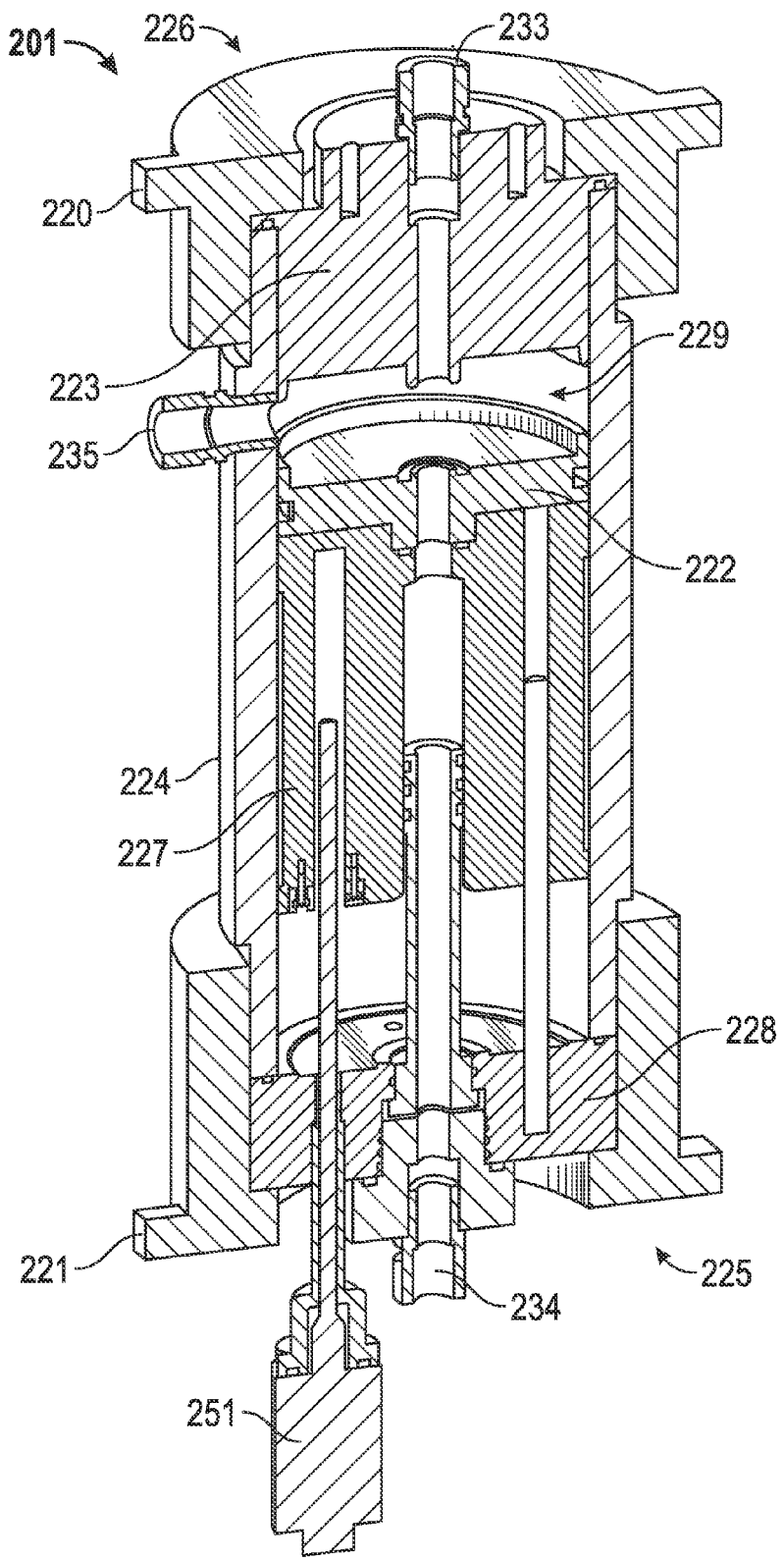
FIG. 2 shows a cross-section view of a vessel according to embodiments of the present disclosure.
Figure 3:
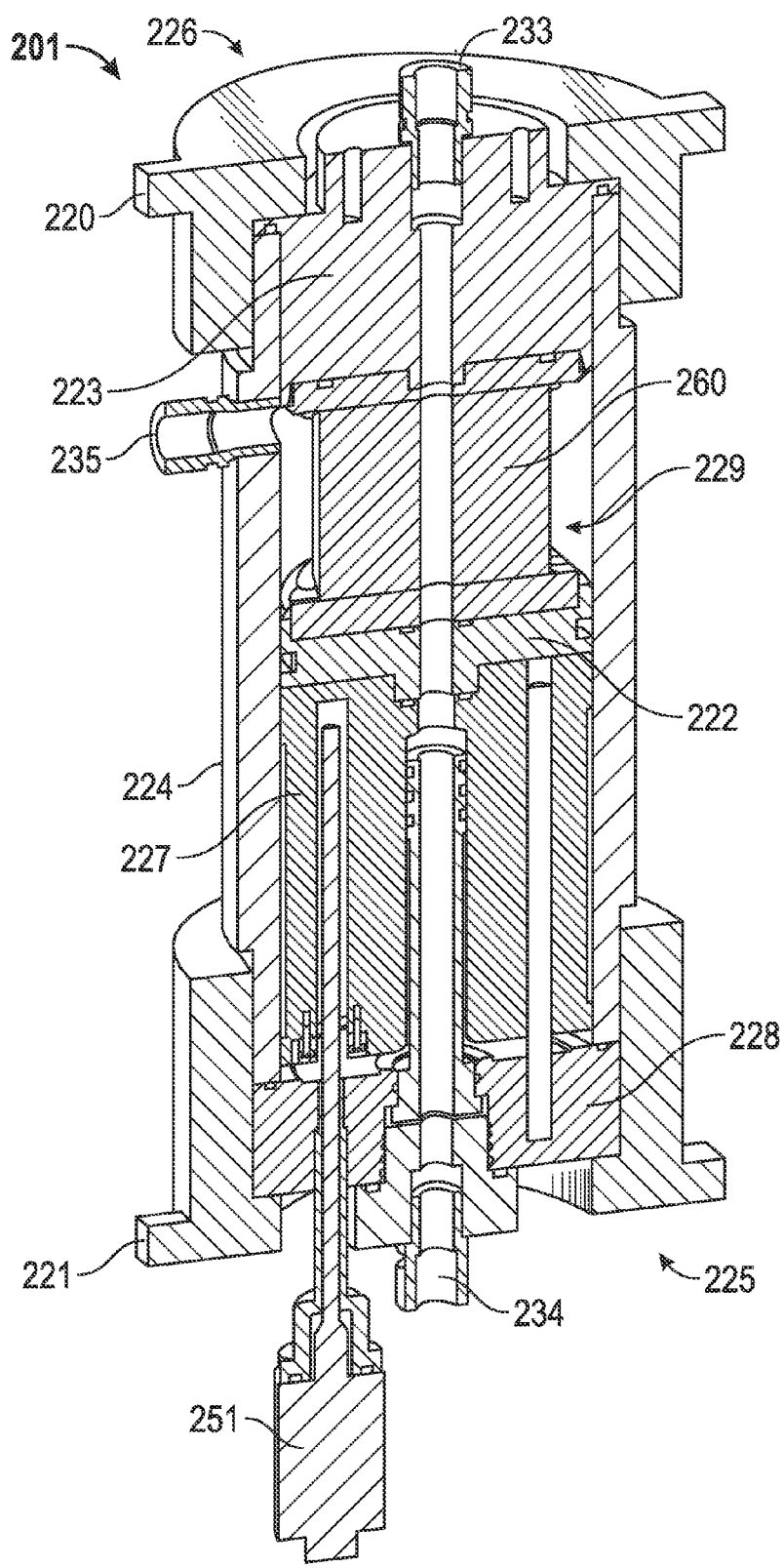
FIG. 3 shows a cross-section view of a vessel having a vertical fracture insert according to embodiments of the present disclosure.

Referring to FIGS. 2 and 3, a cross-section view of a vessel 201, according to embodiments of the present disclosure, is shown. Vessel 201 may include a pressure chamber 224, an upper cap 221, and a lower cap 220. As illustrated, pressure chamber 224 is sealed on a first end 225 by upper cap 221 and sealed on a second end 226 by lower cap 220. A material that may be used to construct pressure chamber 224, upper cap 221, and lower cap 220 includes, for example, alloy steel. However, those of ordinary skill in the art will appreciate that other materials may be used that are both sealable and that withstand the pressure requirements of vessel 201. Examples of types of sealing engagement between upper cap 221, lower cap 220, and pressure chamber 224 include threadable and/or slidably engaging connections. In a threadable connection, an inner diameter of upper cap 221 or lower cap 220 may be configured to threadably engage an outer diameter of pressure chamber 224 to provide a sealed system that prevents the escape of fluids and gasses. In a slidably engaging system, pressure chamber 224 may include ratcheting ends (not shown) that slidably engage ratchet ends of upper cap 221 or lower cap 220. To further enhance the sealability of vessel 201, thereby preventing the escape of gases and fluids therefrom, additional components may be used including, for example, one or more seals (not shown) disposed along the outer diameter of pressure chamber 224. Those of ordinary skill in the art will appreciate that the method of constructing the body of vessel 201 is exemplary, and not a limitation on the scope of the present disclosure.

Vessel 201 may also include a piston 227 disposed inside vessel 201 between an upper pressure plate 228 and an upper sleeve 222. Upper pressure plate 228, in one embodiment, may be constructed from grade stainless steel and forms a sealing barrier between upper cap 221 and piston 227.

Piston 227 is slidably disposed inside pressure chamber 224, and is movable to control a variable sized test chamber 229 between upper sleeve 222 and lower sleeve 223. Piston 227 may be constructed from, for example, 7075 grade aluminum, and may have inner chamber for the insertion of linear transducers 251 therein. Upper sleeve 222 and lower sleeve 223 may be constructed from 304 grade stainless steel. Lower sleeve 223 is disposed inside pressure chamber 224 and forms a sealing engagement with bottom cap 221.

As illustrated in FIG. 3, test chamber 229 may provide space for placement of any variety of test specimens (not illustrated), including fracture inserts and media plates, for example, each of which will be described in more detail below. Movement of piston 227 thus provides for flexibility in the test vessel 201 to test a wide variety of drilling fluids and to simulate any number of formations, including vertical fractures, horizontal fractures, and others as may be envisioned by one of ordinary skill in the art. Those of ordinary skill in the art will appreciate that the size of test chamber 229 may be adjustable by moving piston 227 inside pressure chamber 224. Movement of piston 227 may occur by, for example, tightening the engagement of upper cap 221 with upper pressure plate 228. In other embodiments, the size of test chamber 229 may be controlled by adjusting a ratcheting mechanism (not shown) between upper sleeve 222 and lower sleeve 223. Those of ordinary skill in the art will appreciate that the mechanism used to control the size of test chamber 229 is not a limitation on the scope of the present disclosure; rather, the ability to control test chamber 229 may further increase the range of fluids and formations vessel 201 may test or simulate.

Vessel 201 may include an inlet 233 in bottom cap 220 providing for fluid flow from a fluid source (discussed above) to the test chamber 229. Vessel 201 may also include a first fluid outlet 234 in upper cap 221 providing for fluid flow from test chamber 229 to a fluid collection device. The fluid recovered via outlet 234 may be a filtrate or pass-through fluid, depending upon test specimen disposed in test chamber 229. A second fluid outlet, filtrate outlet 235, may also be provided to provide for fluid flow from test chamber 229 to a fluid collection device, which may be the same or different than that used to collect fluid from outlet 234. One or more additional pressure fluid inlets, fluid inlets, filtrate outlets, or other conduits (not illustrated) may also be disposed through upper or bottom caps 220, 221 to provide for piston movement control, filtrate collection, location of measurement devices, etc.

As illustrated in FIG. 3, a fracture insert 260 may be disposed within chamber 229 for testing the performance of a fluid. Examples of a fracture insert 260 are illustrated in FIGS. 4A (side elevation view), 4B (side view), 4C (cross-sectional view), and 4D (top-view).

Referring now to FIGS. 4A-4C, a fracture insert 260 may include a top head 402, a bottom head 404 (respective end caps), and at least one cylindrical portion 406. As used herein, "cylindrical" refers to the "portions" as having a general shape representative of a section of a cylinder, such as a cylinder cut by one, two, or more planes parallel to the cylinder axis, although other variations are envisioned as discussed below to provide for the simulation of various fracture configurations. Top head 402 and bottom head 404 may be coupled to cylindrical portions 406 via screws 408 or other devices to hold cylindrical portions 406 in place during testing. A ring 410 may also be provided to effect a seal between top head 402 and upper sleeve 222 (similar for bottom head 404, if necessary).

When the fracture insert 260 is assembled, the cylindrical portions 406 are aligned opposite one another and define two or more radial gaps 412 therebetween. In one embodiment, a vertical fracture insert 260 may be inserted into the chamber 229. Additionally, the cylindrical portions 406, along with respective openings through top and bottom heads 402, 404, define an axial flow channel 416 from the top to the bottom of the vertical fracture insert 260. The radial gaps 412 provide a flow path from the axial flow channel 416 to a radial terminus 420 of the cylindrical portions 406.

FIGS. 4A-4D illustrate fracture insert 260 as including two hemicylindrical portions 406, providing for two radial flow channels from the axial flow channel 416 to the radial terminus 420. In other embodiments, three, four, or more cylindrical portions 406 may be used, defining three, four, or more radial gaps and/or flow channels therebetween.

The radial gaps 412 formed by the respective cylindrical portions may have a constant or variable width in the range from about 0.1 mm to about 10 mm. In some embodiments, a maximum width of the radial gaps may be in the range from about 0.1 to about 10 mm; from about 1 mm to about 7.5 mm in other embodiments; and from about 2 mm to about 5 mm in yet other embodiments.

Figure 6:
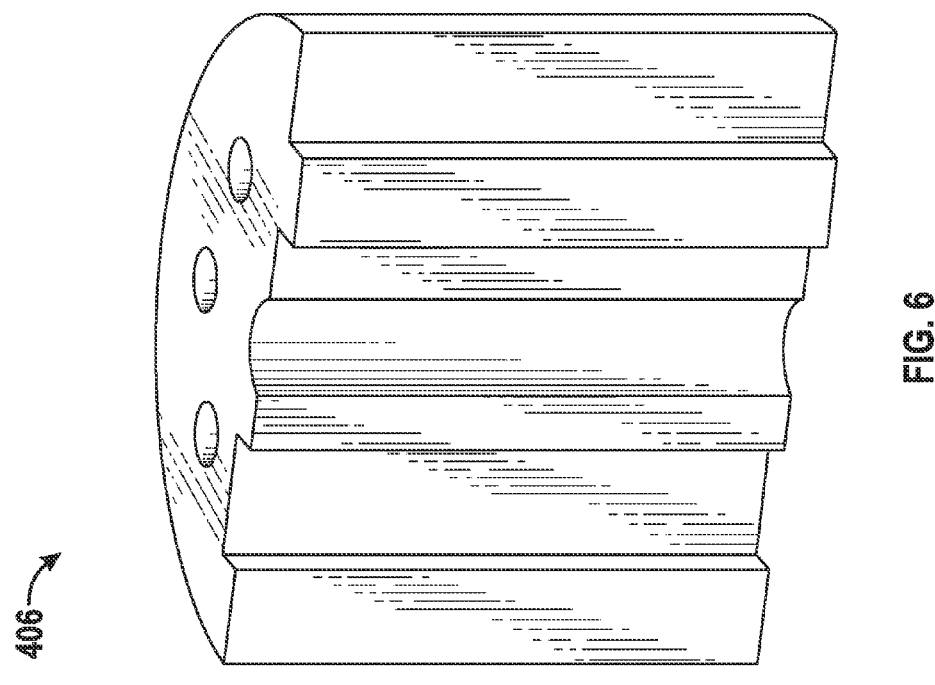
FIGS. 5-7 show side profile views of various fracture inserts according to embodiments of the present disclosure.
Figure 5:
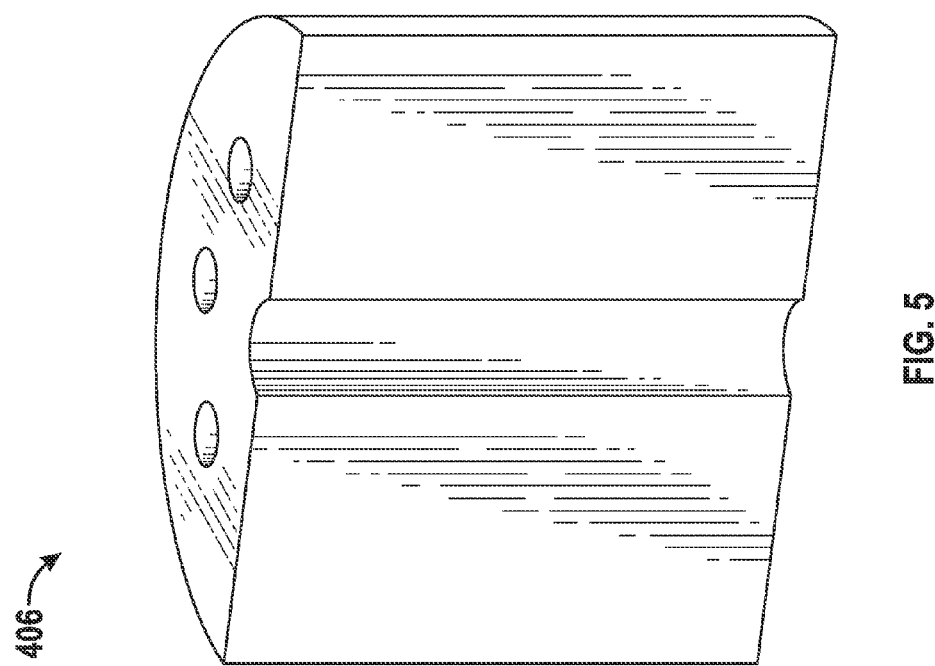
Figure 7:
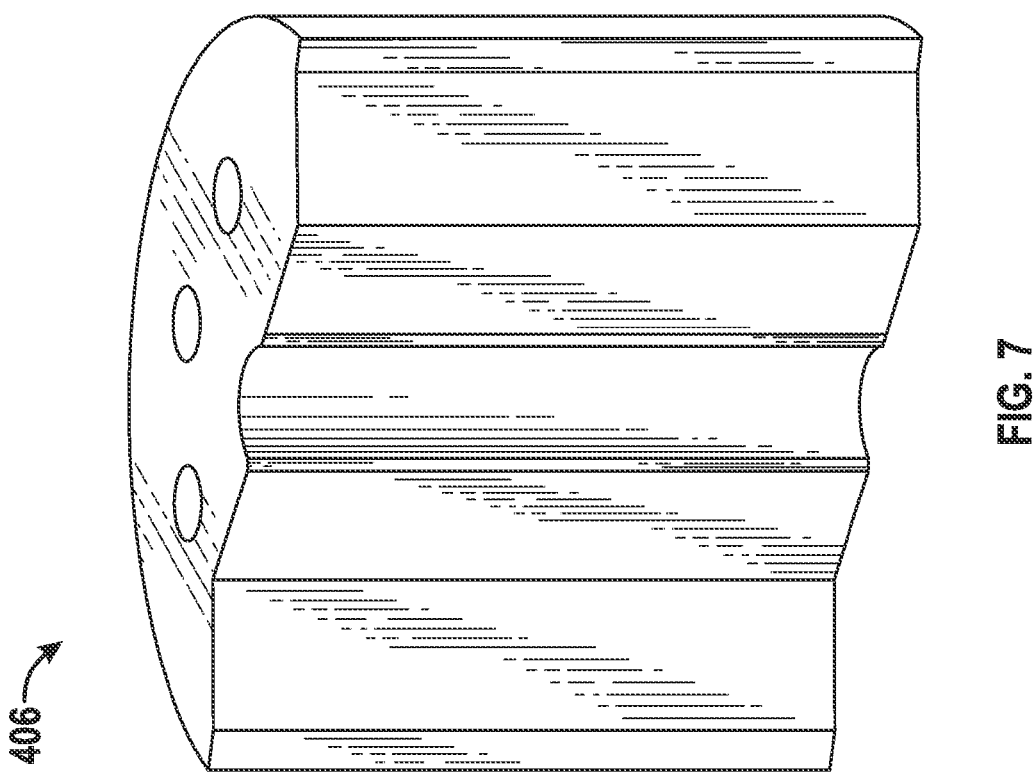

The radial flow channel(s) may extend the entire height of the cylindrical portions 406 or only a portion thereof. The axial length (height) of the radial flow channel(s) may be, for example, in the range from about 1 mm to about 150 mm, such as within the range from about 50 mm to about 100 mm. The meshing or clearance provided by various sections of the cylindrical portions may also provide for two or more radial flow channels spaced axially along the height of the fracture insert. In some embodiments, the radial flow channel may be substantially perpendicular to the axial flow channel; non-perpendicular in other embodiments. The inserts disclosed herein may allow for flow substantially perpendicular to a fracture orientation. The radial flow channel may include parallel sides, non-parallel sides (i.e., a tapered flow path), a straight flow path, or a tortuous flow path that may meander up, down, sideways, etc., with respect to the axial flow channel. The tortuous flow path may include, for example, radial bends (such as a gentle turn, greater or less than 90° overall), 90° turns, and sharp angle turns (>90° bends), as well as other configurations that may be envisioned by those skilled in the art and desiring to emulate possible fracture configurations as may be encountered while drilling a subterranean formation. FIGS. 5-7 illustrate a few of these possibilities.

The cylindrical portions of the fracture inserts may be made from any material, such as aluminum or a steel, among others. In some embodiments, the fracture inserts may be formed as a block of material, a hollow shell having a solid exterior. In other embodiments, the cylindrical portions of the fracture inserts may be formed of a porous material, allowing testing of the performance of a fluid loss control fluid in a fractured and porous substrate.

Referring again to FIG. 3, the vessel 201 for testing a drilling fluid, as assembled, may thus include a fluid inlet 233, a filtrate outlet 235, a fluid outlet 234, and a fracture insert 260 disposed within the vessel, such as in test chamber 229. As assembled, the vertical fracture insert includes two or more cylindrical portions defining radial gaps therebetween and forming an axial flow channel 416. The radial gaps define a flow channel from the axial flow channel to the radial terminus 420 of the vertical fracture insert and to the filtrate outlet 235.

In operation, a test fluid, such as a drilling fluid having a fluid loss control material, is fed from a test fluid container (FIG. 1) and introduced to vessel 201 via fluid inlet 233. The test fluid then flows into the axial flow channel 416, where a portion of the test fluid may pass through axial channel 416 and be recovered via fluid outlet 234. Due to the vertical fracture, a portion of the test fluid may flow through the radial gaps 412 (vertical fractures) from the axial flow channel 416 to the radial terminus 420 of the fracture insert and thence recovered via filtrate outlet 235.

During the test, fluid loss control material may accumulate within or at the entrance to the vertical fracture (i.e., radial gap 412), restricting flow of fluid from the axial flow channel 416 to filtrate outlet 235. The measured amount of fluid loss through the vertical fracture and the amount of time required for the fluid loss control material may then be used to assess the performance of the test fluid for plugging the vertical fracture.

Axial flow path 416 may also provide for additional tests to be run. For example, the test fluid, such as a fluid loss control fluid, may be used to plug or partially plug the vertical fracture with a fluid loss control material, forming a filter cake. The flow of the test fluid may then be stopped, and a second test fluid, such as a drilling fluid or a breaker fluid, may then be introduced via inlet 233 to simulate resumption of drilling operations after the fracture has been plugged, continuing drilling operations during a fluid loss situation, or breaking of the filter cake formed by the fluid loss control medium, such as with a breaker fluid, as well as many other drilling operations as may be envisioned by those skilled in the art. Testing of resumed drilling operations, for example, may be used to investigate performance of the fluid loss control material in response to increased or decreased pressures, changes in compositions, and other variables as may be encountered when drilling operations are resumed.

Multiple tests with the same fracture insert may be run, including operations at similar test conditions (verification runs), or different test conditions (varied flow rate, pressure, temperature, etc.).

It may also be desirable to test the performance the test fluid over a wide array of fracture widths, fracture tortuosities, etc. In such instances, the fracture insert may be removed from vessel 201, and replaced with a different fracture insert (i.e., replacing the entire fracture insert assembly, including all cylindrical portions). Alternatively, a portion of the fracture insert, such as one or more of the cylindrical portions, may be removed and replaced to provide a radial gap having differing dimensions (gap width, tortuosity, etc.). The fracture insert may then be reinserted into the test vessel and further testing may be performed.

In some embodiments, such as where two, three, four, or more cylindrical portions are used, the gaps formed by the respective opposing cylindrical portions may or may not be of equivalent dimensions (gap width, tortuosity, etc.), allowing for the performance of a test fluid with varied fracture sizes, as may be encountered in subterranean formations, to be analyzed.

As illustrated in FIG. 3, a fracture insert 260 according to embodiments herein is shown disposed between upper and lower sleeves 222, 223. The vessel may also be used to test other inserts, such as media plates (e.g., porous, impermeable plates, etc.) as described in U.S. Pat. No. 7,900,504, which is incorporated herein in its entirety. When desired to test the performance of a fluid in a porous medium, a fracture insert may be removed from the vessel and a media plate inserted into test chamber 229 for testing as described in U.S. Pat. No. 7,900,504. Thus, the present test vessel may be used to test both vertical fractures as well as horizontal fractures. The flexibility provided by the present test apparatus may thus allow for full and complete characterization of loss control fluids and loss control materials, including performance for treating various solid or porous fractured formations and resumption of drilling, as discussed above.

Operationally, embodiments of the present disclosure may be used to test and determine sealing characteristics of a drilling fluid. Subsequently, the sealing characteristics, and the data obtained from the testing, may be used to optimize a drilling fluid for drilling through a given formation.

Figure 8:
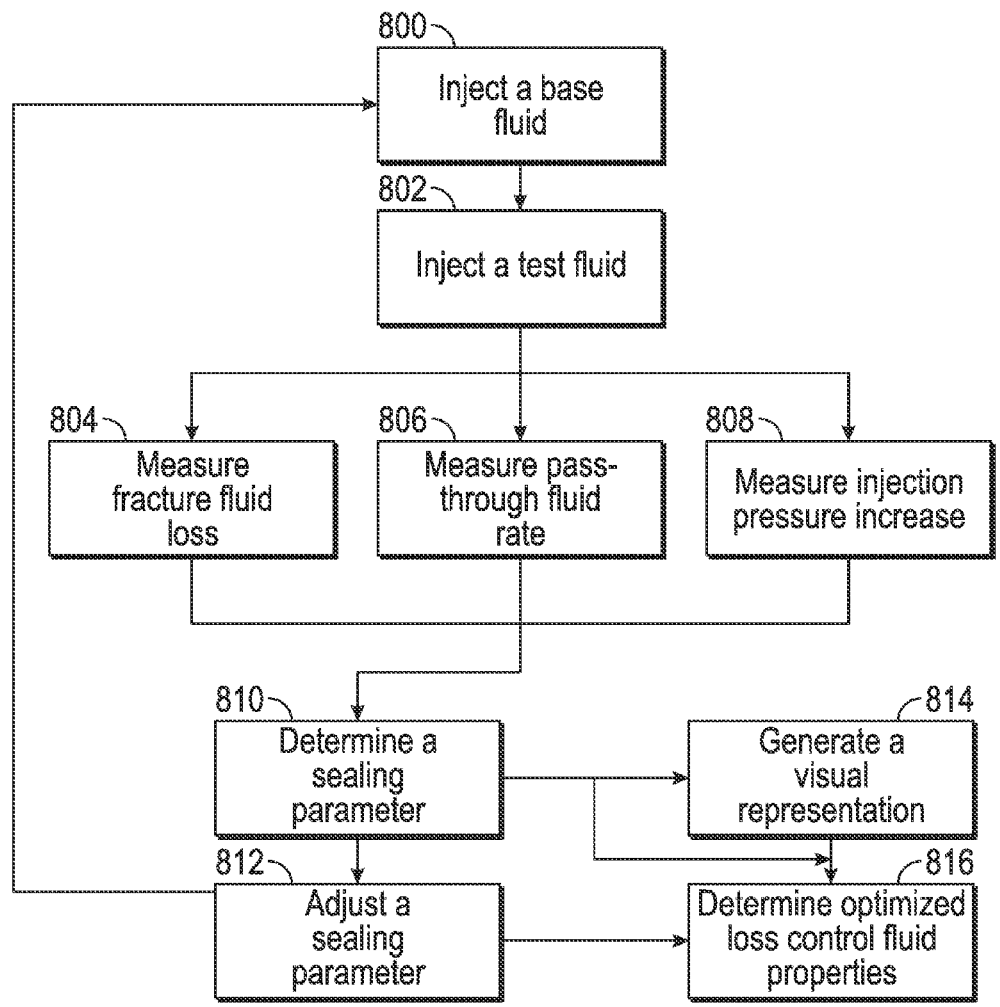
FIG. 8 shows a flow chart of a method for determining sealing characteristics and for optimizing a drilling fluid according to embodiments of the present disclosure.

Referring to FIG. 8, a flow chart of a method for determining sealing characteristics and for optimizing a drilling fluid is shown. In this embodiment, a base fluid generally including, for example, a water-based or oil-based fluid of a known viscosity and known properties, is injected 800 from a fluids container into a vessel, as described above. The base fluid may be used to determine a base flow rate and to pressurize the equipment for the test fluid.

After the system is pressurized by injecting 800 the base fluid, a test fluid is injected 802 from a test fluid container. The test fluid may include a water-based or oil-based fluid including fluid loss control material of a known particle size. Examples of fluid loss control materials that may be tested includes sized graphite, barite, calcium carbonate, ground nut, and other fluid loss control material as are known to those of ordinary skill in the art. The test fluid generally contains a known concentration of fluid loss control material and is injected 802 under a known pressure. As such, a rate flow of the test fluid though the vessel will be known. Injection 802 continues under known pressure and flow rate conditions, and the fluid is substantially continuously injected into a fluids inlet of the vessel.

Inside the vessel, the fluid may contact the fracture inserts, and by following a path of least resistance travels through a gap between cylindrical portions, as described above. As the fluid passes through the gap, the fluid may adhere to the sidewalls of the cylindrical portions, and the fluid loss control material may block fluid flow through the gap. However, some of the fluid may pass through the filtrate outlet and into a collection container. The volume of fluid flowing into the collection container may then be measured 804, by a sensor 111 or pump 108c, for example. As such, a measured fracture fluid loss is determined. The amount of fluid lost through the gap may be used later in the process for determining sealing properties of fluid loss control material and/or drilling fluids in general.

Contemporaneous with the measuring 804 of a fracture fluid loss, a portion of the drill fluid including fluid loss control material entrained therein may flow through the axial channel to the fluid outlet. As the fluid loss control material builds in the fracture, the flow of fluids through the fluid outlet may increase, and the flow rate into the vessel via the inlet may eventually equal the flow rate of the fluid exiting via the fluid outlet, indicating full pluggage of the fracture. The volume of fluid flowing through the fluid outlet and into a collection container may be measured 806 by sensor 111 or pump 108b, for example. The amount of fluid passing through the axial channel, and any changes in properties thereof (e.g., loss control material concentration, etc.) may be used later in the testing to determine sealing properties of fluid loss control materials and/or drilling fluids in general.

As the measurements of fluid loss, fluid pass-through, and injection pressure increases 808 are determined, a data acquisition system, as described above, may be recording and collecting data from the system. For example, a sensor 111 may send a voltage or data signal to the data acquisition system which may then integrate all collected data into a single program to display as a spreadsheet, database, or the like. Examples of such collected data may include the pressures, back pressures, fluid flow rates, fluid densities, fluid component concentrations, and temperatures of the system. For data pertaining to volumes, pumps 108a-d may serve as a sensor. In another example, to collect data pertaining to pressure, a pressure transducer (not shown) may serve as a sensor. In yet another example, for data related to fracture width, a linear transducer may serve as a sensor. This data may later be used to determine, for example, a time interval at which a certain fluid loss control material began affecting the transmittance of fluids through the fracture.

After collecting all necessary data, including measuring a fracture fluid loss, a sealing parameter of the test fluid is determined 810. An evaluation of sealing parameter may be based on factors such as whether pressure can be built or increased, amount of fluid loss through a fracture, and/or LCM cake thickness, for example. Examples of sealing parameters that may be determined for a fluid include a seal location, a fracture closure pressure, an effective particle size, a fluid loss reduction, and/or a maximum sealing pressure. Those of ordinary skill in the art will appreciate that additional sealing parameters may also be determined that are based on, for example, viscosities of the fluid and/or sealing times, as well as properties of the seal based on resumed drilling operations and others as discussed above.

In other embodiments, a determined sealing parameter may include determination of a particle size of a fluid loss control material that may be useful for a given fracture width. Once the fracture seal location is determined, as described above, a particle size may be optimized to optimally control the flow of fluids through a formation of a known fracture size. Thus, in the optimization of a drilling fluid, the sealing properties of a drilling fluid for a fractured formation may be compensated for by adjusting fluid loss control material particle size appropriately.

Those of ordinary skill in the art will appreciate that the particle size adjustments may provide a drilling operator the ability to reduce fluid loss to a specified level and determine a sealing pressure appropriate for a known formation, fluid, particle size, or other drilling parameter. Furthermore, the sealing parameters described herein are merely exemplary; additional conditions may be modeled by embodiments of the present disclosure to further analyze fracture size and leak-off rates (both to a fracture and a porous matrix).

Still referring to FIG. 8, after a sealing parameter is determined, an operator may conclude the test by outputting and/or visually representing 814 the collected data and/or determined sealing parameters. Generally, a visual representation may include numerical, graphical, or pictoral representations of the collected and/or determined data. Such representations may be output to a display, information processor screen, printed on paper, or otherwise stored in a database for further analysis.

In certain embodiments, an operator may decide after determining a sealing parameter 810 that the fluid could be optimized by changing a variable in the drilling fluid. Thus, the operator may adjust a sealing parameter 812 of the fluid and re-run the test. Examples of parameters that the operator may adjust include a viscosity, a flow-rate, a pressure, a back pressure, a fluid loss control fluid particle size, loss control material types, adding additional fluid loss control fluids, or changing other parameters of the system as would be known to those of skill in the art.

After a parameter of the fluid is adjusted 812, such as a particle size of a fluid loss control material, the test may be restarted by repeating the injecting 800 and/or 802, the measuring 804, 806, and 808 and determining 810 until the fluid is optimized 816. Optimization depends on the conditions an operator may be trying to achieve; however, examples of optimization may include when a drilling fluid seals within a given time interval, under a certain pressure or temperature, or under a certain fluid flow rate. Additionally, optimization may include optimizing a specified sealing parameter. Thus, in some embodiments, a fluid loss control material particle size may be optimized for a specified fracture width or in consideration of specific formation porosity.

Figure 9:
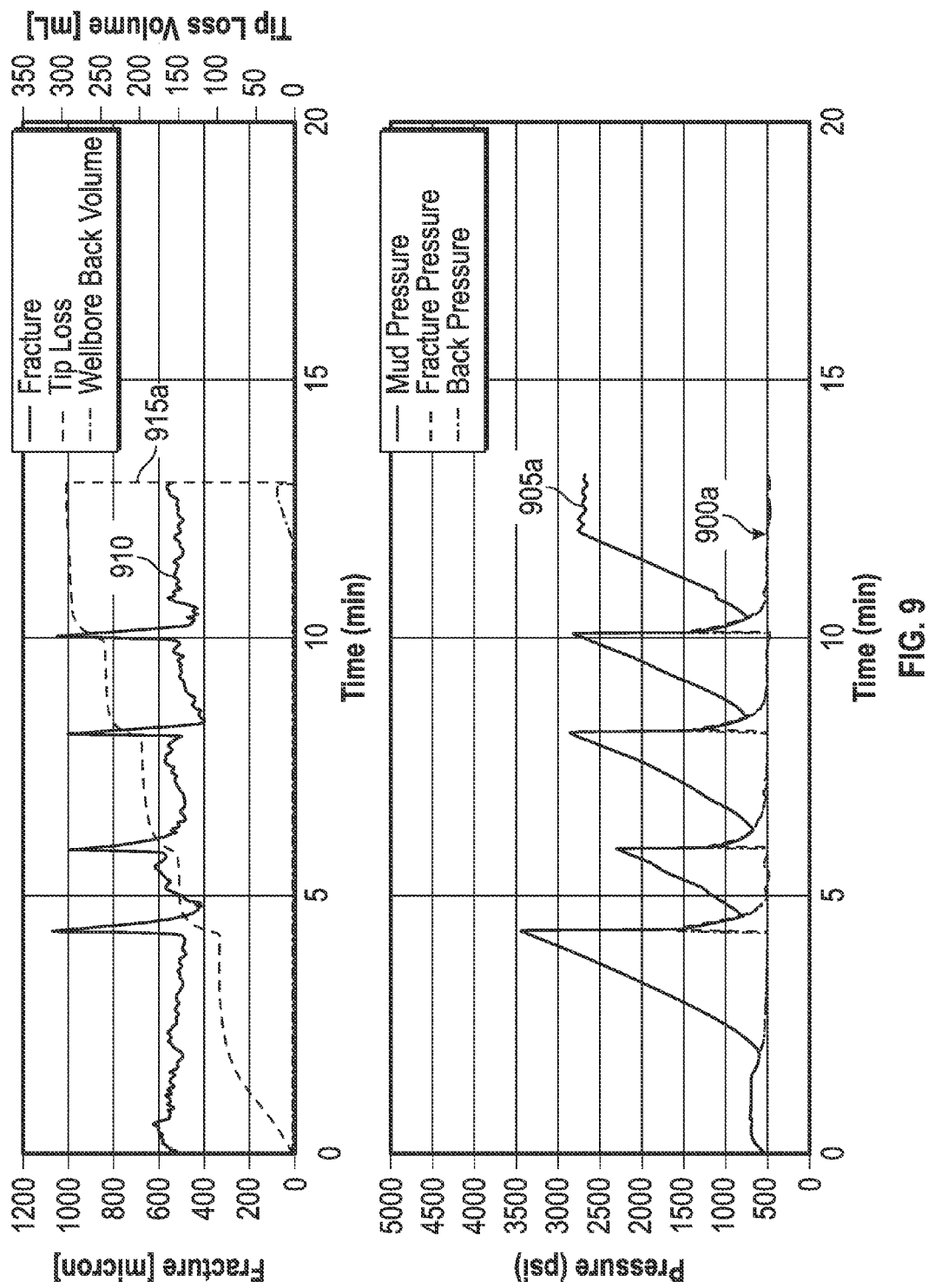
FIGS. 9-11 show visual representations of facture test data generated according to embodiments of the present disclosure.
Figure 10:
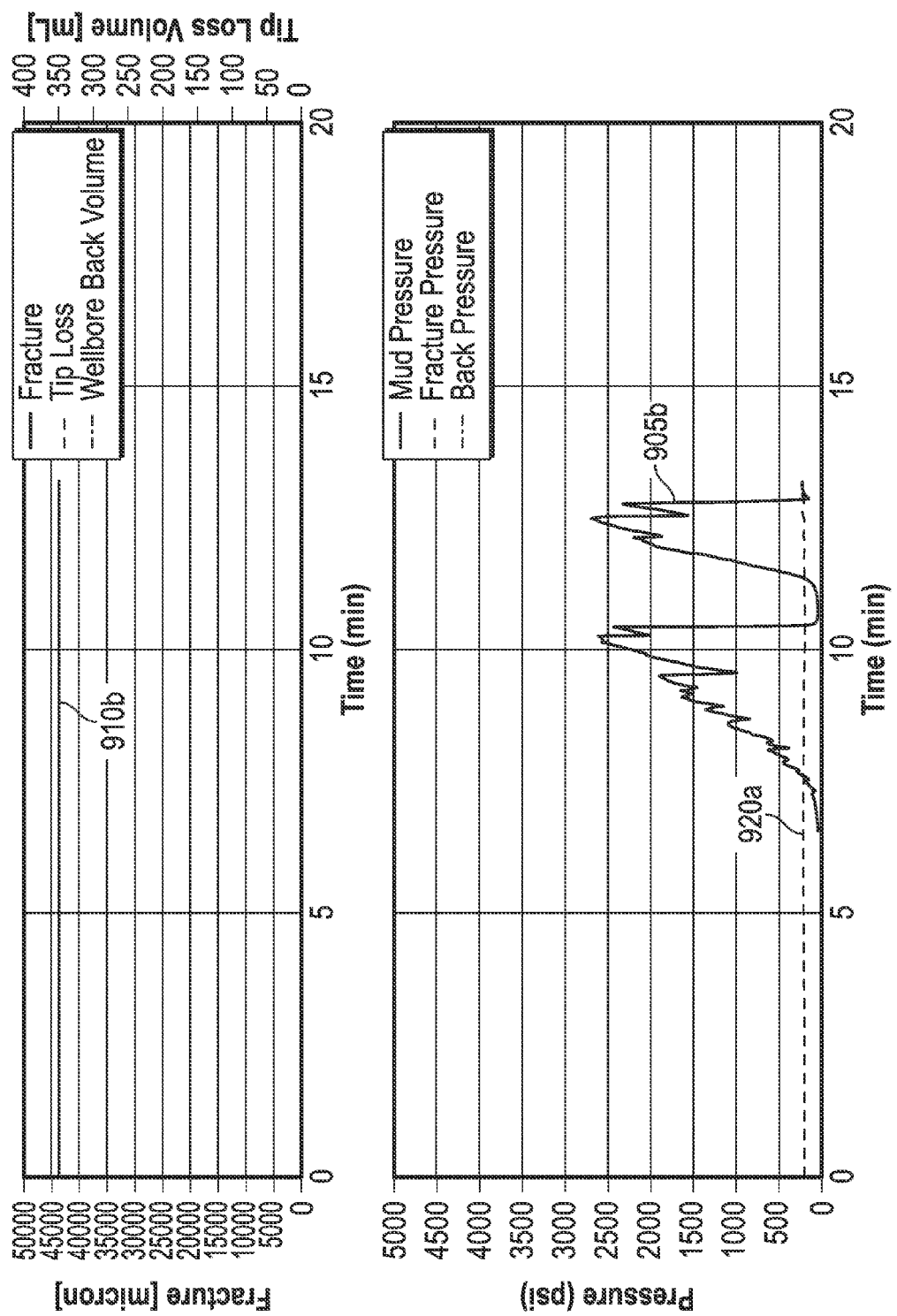
Figure 11:
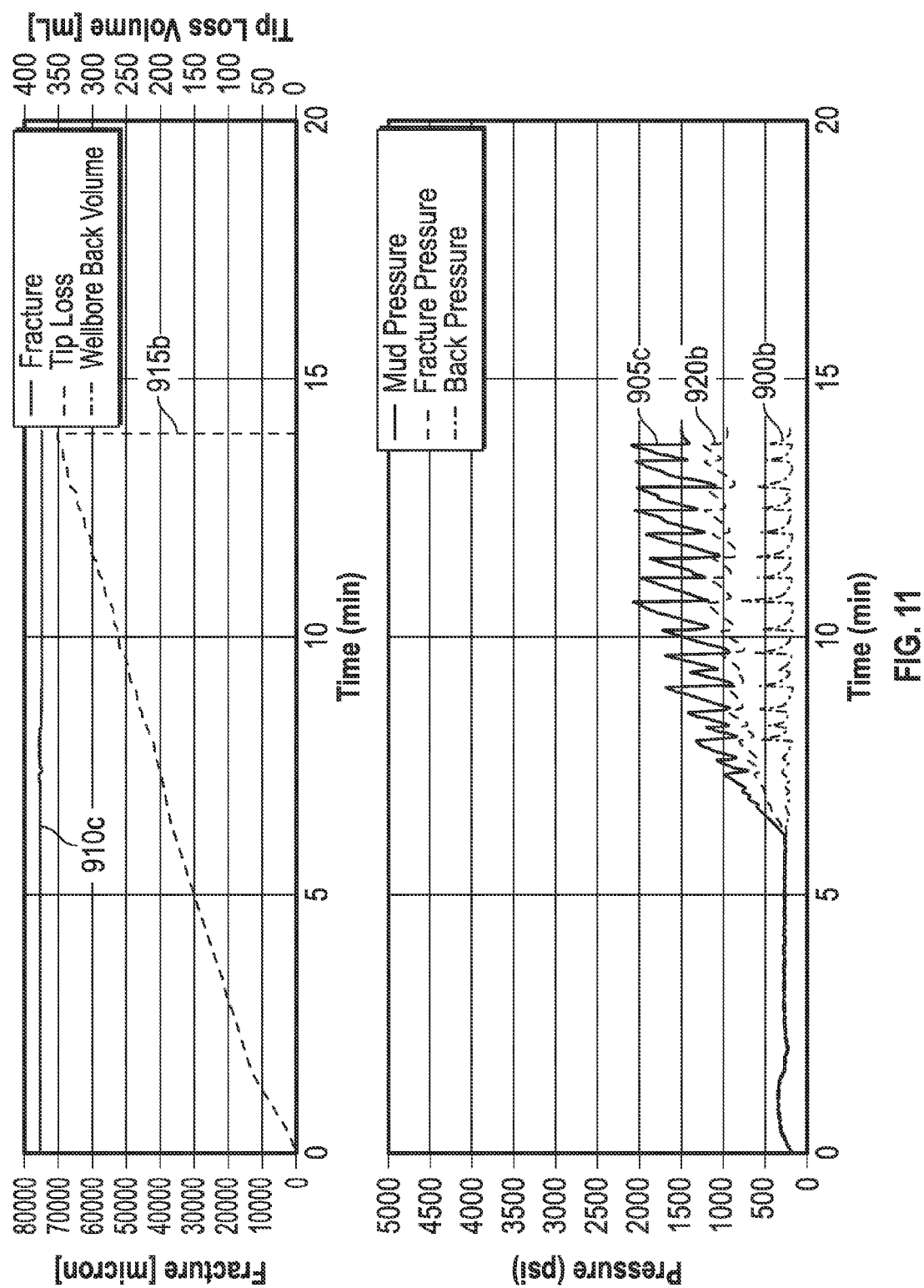

Referring now to FIGS. 9-11, visual representations of data collected during tests of a fluid in accordance with embodiments of the present disclosure are shown. The tests may include analysis of back pressure 900a-b, test fluid pressure ("mud pressure) 905*a-c*, fracture width 910*a-c*, mud volume to tip ("conductivity loss") 915*a-b*, wellbore back volume 920*a*, and facture closure pressure 925*a-c*.

Those of ordinary skill in the art will appreciate that FIGS. 9-11 only depict examples of possible outcomes of testing using systems and methods in accordance with the present disclosure. In other embodiments, the tests may include additional visual presentations of data and/or data sets compiled by a data acquisition system or information processor, and may include a detailed analysis of varied properties of fluid loss control materials. Examples of such visual representations and/or studies that may be generated using systems and methods of the present disclosure may include a comparison of permeable fracture tests at varying back pressures 900*a-b*, as shown in FIG. 9-11.

Generally, mud pressure 905*a-c* may be interpreted as the sealing pressure on the wellbore side of a fracture. As a bridge is formed, mud pressure 905*a-c* may increase. Fluid pressure may continue to increase until it reaches a maximum operating pressure, such as approximately 6000 psi. As shown in FIG. 9, for example, increases in back pressure 900*a* may result in a corresponding spike or increases in mud pressure 905*a*. Regarding fluid loss 915*a*, the value of each increases steadily with time as whole mud is lost to the fracture. Once an initial bridge forms, load-off may be reduced and the slope of the line may flatten out. A reduction in the slope of the line associated with fluid loss 915*a* corresponds to the building of a fracture seal and with it an accompanying reduction in fluid loss to the fracture. Referring to the fracture width, indicated by 910*a*, as the test fluid pressure builds, and while the fracture seal formed remains in place, the fracture width 910*a* may be held steady (within design parameters) until the seal breaks. A break is indicated by a drop in fluid pressure combined with an increase in fracture width 910*a* as pumps compensate. Upon failure, fracture width 910*a* may return to the initial point and the mud pressure 905*a* begins to rise again as a new seal forms.

FIG. 10 depicts a fracture evaluation with no back pressure present. To attain no back pressure, a pump may be disconnected or decoupled from any outlet of vessel 201. As such, any flow through fluid flows directly through the vessel 201 thus generating an evaluation depicting constant fracture width 910*b*.

Moving now to FIG. 11, a fracture evaluation with increasing pressure, such as back pressure 900*b*, fracture pressure 920*b*, and mud pressure 905*c*, is shown. Pressure may be applied to vessel 201 via an accumulator and/or pump (not shown) coupled to an outlet. Both the pump and fluid may be pressured, to 250 psi for example, resulting in increasing peaks of the previously mentioned pressures. With increasing pressure, fluid loss 915*b* gradually increases while fracture width 910*c* is shown to remain constant.

Embodiments of the present disclosure may provide systems and methods for testing and evaluating drilling fluids and fluid loss control materials through fractured formations. Embodiments disclosure herein may provide methods for assessing the effectiveness of fluid loss control materials in sealing permeable and/or impermeable fractures. Furthermore, the system and methods may inexpensively and rapidly test the sealing effectiveness of various fluid loss control materials as well as provide a way to control and measure changes in fracture width in formation.

Also, the systems and methods disclosed herein may allow an operator to optimize fluid loss control materials types and concentrations for specific fracture widths, as well as providing an indication of propped width within sealed fractures caused by fluid loss control materials that have been pressed into the fractured. Finally, embodiments of the present disclosure may allow an operator to test and optimize drilling fluids and fluid loss control materials under higher pressures with greater precision. Such tests may further provide an operator the ability to measure two discrete fluid streams, specifically, through the fracture and across the fractured formation (i.e., pass-through from borehole to surface), to optimize drilling fluids for drilling in permeable and/or fractured formation.

Further, the systems and methods disclosed herein may provide for the simulation of systems having large fractures, such as up to about 5 or 6 mm fractures, as well as the ability to simulate resuming drilling operations after a fracture has been plugged or continuing drilling operations during a partial or reduced fluid loss situation.

The fracture inserts as described above may be described and used in various aspects and/or embodiments. In an aspect of the present disclosure, a fracture insert may include a first cylindrical portion and a second cylindrical portion disposed opposite the first cylindrical portion defining a radial gap therebetween to form an axial flow channel. The axial flow channel may provide a flow path for a drilling fluid from a top of the cylindrical portions to a bottom of the cylindrical portions. The radial gap may provide a flow path for the drilling fluid from the axial flow channel to a radial terminus of the first cylindrical portion and the second cylindrical portion.

In one embodiment, a fracture insert disclosed herein may include at least one end cap coupled to the first cylindrical portion and the second cylindrical portion to prevent movement of the cylindrical portions when the insert is in use. In another embodiment, the first cylindrical portion and the second cylindrical portion of a fracture insert disclosed herein are hemicylindrical defining two radial gaps from the axial flow channel to the radial terminus of the fracture insert. In yet another embodiment, the radial gap defined within a fracture insert disclosed herein may be parallel, non-parallel, straight, tortuous, or combinations thereof. In yet another embodiment, the axial flow channel defined within a fracture insert disclosed herein may provide for flow substantially perpendicular to flow through the radial gap previously mentioned.

In one embodiment, the radial gap defined within a fracture insert disclosed herein may have a width within a range from about 0.1 mm to about 5 mm. In another embodiment, the radial gap defined within a fracture insert disclosed herein may have a width within a range from about 2 mm to about 5 mm. In another embodiment, the radial gap defined within a fracture insert disclosed herein may be tortuous and include at least one of radial turns, 90° turns, and sharp angle turns. In yet another embodiment, an axial length of the radial gap may be within a range from about 1 mm to about 150 mm. In yet another embodiment, an axial length of the radial gap may be within a range from about 50 mm to about 100.

In another aspect of the present disclosure, a vessel for testing a drilling fluid may include an inlet for receiving a drilling fluid, a filtrate outlet, and a fluid outlet. The vessel may further include a fracture insert disposed within the vessel, the insert including a first cylindrical portion opposite a second cylindrical portion defining a radial gap therebetween and forming an axial flow channel. The axial flow channel may provide a flow path for the drilling fluid from the inlet to the outlet and the radial gap may provide a flow path for the drilling fluid from the inlet to the outlet.

In one embodiment of the vessel, the first cylindrical portion and the second cylindrical portion of the fracture insert may be hemicylindrical defining two radial gaps from the axial flow channel to a radial terminus of the insert. In another embodiment of the vessel, the radial gap may be parallel, non-parallel, straight, tortuous, or combinations thereof. In yet another embodiment of the vessel, the axial flow channel defined within a fracture insert disclosed herein may provide for flow substantially perpendicular to flow through the radial gap previously mentioned.

In one embodiment, the radial gap defined within a fracture insert of a vessel disclosed herein may have a width within a range from about 0.1 mm to about 5 mm. In another embodiment, the radial gap defined within a fracture insert of a vessel disclosed herein may have a width within a range from about 2 mm to about 5 mm. In another embodiment, the radial gap defined within a fracture insert of a vessel disclosed herein may be tortuous and include at least one of radial turns, 90° turns, and sharp angle turns. In yet another embodiment, an axial length of the radial gap may be within a range from about 1 mm to about 150 mm. In yet another embodiment, an axial length of the radial gap may be within a range from about 50 mm to about 100.

In another aspect of the present disclosure, a system for testing a drilling fluid may include vessel with an inlet for receiving a drilling fluid, a filtrate outlet, and a fluid outlet. A fracture insert may be disposed within the vessel, the insert including a first cylindrical portion opposite a second cylindrical portion defining a radial gap therebetween and forming an axial flow channel. The axial flow channel may provide a flow path from the inlet to the fluid outlet and the radial gap may provide a flow path from the inlet to the filtrate outlet. The system may further include a base fluid container in fluid communication with the inlet, a test fluid container in fluid communication with the inlet, a filtrate container in fluid communication with the filtrate outlet, and/or a collection container in fluid communication with the fluid outlet.

In one embodiment of the system, a radial gap may be parallel, non-parallel, straight, tortuous, or combinations thereof. In another embodiment of the system, the first cylindrical portion and the second cylindrical portion are hemicylindrical defining two radial gaps from the axial flow channel to a radial terminus of the fracture insert. In another embodiment, the system for testing a drilling fluid disclosed herein may include a data acquisition system to receive data from at least one of the vessel, the fluid container, the filtrate container, and the collection container. In yet another embodiment of the system, the axial flow channel defined within a fracture insert disclosed herein may provide for flow substantially perpendicular to flow through the radial gap previously mentioned. In yet another embodiment, the system for testing a drilling fluid may include a third cylindrical portion and a fourth cylindrical portion, defining three or four radial gaps, respectively, from the axial flow channel to a radial terminus of the fracture insert.

In one embodiment, the radial gap defined within a fracture insert of a system disclosed herein may have a width within a range from about 0.1 mm to about 5 mm. In another embodiment, the radial gap defined within a fracture insert of a system disclosed herein may have a width within a range from about 2 mm to about 5 mm. In another embodiment, the radial gap defined within a fracture insert of a system disclosed herein may be tortuous and include at least one of radial turns, 90° turns, and sharp angle turns. In yet another embodiment, an axial length of the radial gap may be within a range from about 1 mm to about 150 mm. In yet another embodiment, an axial length of the radial gap may be within a range from about 50 mm to about 100 mm.

Another aspect of the present disclosure is a method for determining sealing characteristics of a drilling fluid including injecting a first test fluid having a fluid loss control material to a vessel including an inlet, a filtrate outlet, and a fluid outlet; a fracture insert disposed within the vessel, the fracture insert including a first cylindrical portion opposite a second cylindrical portion defining a first radial gap therebetween and forming an axial flow channel. The axial flow channel may provide a flow path from the inlet to the fluid outlet and the first gap may provide a flow path from the inlet to the filtrate outlet. The method for determining sealing characteristics of a drilling fluid may include measuring a fluid loss through the first radial gap. The method may further include stopping a flow of the first test fluid following at least a partial plugging of the first radial gap with the fluid loss control material. The method for determining sealing characteristics may further include injecting a second test fluid to the vessel to simulate at least one of: (1) resuming drilling operations after the first radial gap has been plugged; (2) continuing drilling operations during a fluid loss situation; and (3) breaking of a filter cake comprising the fluid loss control material using a breaker fluid. The method for determining sealing characteristics may further include at least one of: (1) removing at least one of the first cylindrical portion and the second cylindrical portion from the vessel; (2) inserting at least one of a third cylindrical portion and a fourth cylindrical portion into the vessel to define a second radial gap therebetween and forming a second axial flow channel; (3) injecting the test fluid having the fluid loss control material from the test fluid container to the vessel; and (4) measuring a fluid loss through the second radial gap.

In another embodiment, the radial gap and the second radial gap of the method for determining sealing characteristics disclosed herein have differences in at least one of a minimum gap width, a maximum gap width, an average gap width, and tortuosity. In another embodiment, the method of determining sealing characteristics may further include determining a sealing parameter based on the fluid loss through the radial gap. In yet another embodiment of the method for determining sealing characteristics, the step of determining the sealing parameter may include determining at least one of a seal location, particle size, reduction of fluid loss, and maximum sealing pressure.

In yet another aspect, a method for optimizing a drilling fluid is disclosed. The method may include injecting a drilling fluid having a first fluid loss control material particle size into a vessel which includes an inlet, a filtrate outlet, a fluid outlet, and a fracture insert disposed within the vessel. The fracture insert may include a first cylindrical portion opposite a second cylindrical portion defining a radial gap therebetween and forming an axial flow channel, the axial flow channel providing a flow path from the fluid inlet to the fluid outlet and the radial gap providing a flow path from the fluid inlet to the filtrate outlet. The method may further include at least one of: (1) measuring a fluid loss through the radial gap, (2) determining a sealing parameter based on the fluid loss, and (3) adjusting the fluid loss control material particle size based on the sealing parameter. The method may further including at least one of: (1) injecting the drilling fluid having the adjusted fluid loss control material particle size into the vessel, and (2) repeating the measuring, determining, adjusting, and injecting until the material particle size of the drilling fluid is optimized.

In one embodiment of the method of optimizing a drilling fluid, the step of adjusting the fluid loss control material particle size based on the sealing parameter may include selecting a sealing parameter from at least one of: (1) a seal location, (2) particle size, (3) reduction of fluid loss, and (4) maximum sealing pressure. In yet another embodiment, the method of optimizing a drilling fluid disclosed herein may further include obtaining data from a remote data source for a current reservoir, the data including at least one of fracture width, fracture tortuosity, drilling fluid type, drilling fluid loss rates, and reservoir pressure; and returning optimized drilling fluid parameters to the remote data source.

Although the preceding description has been described herein with reference to particular means, materials, and embodiments, it is not intended to be limited to the particulars disclosed herein; rather, it extends to all functionally equivalent structures, methods, and uses, such as are within the scope of the appended claims.

What is claimed is:

1. A fracture insert comprising:
a first cylindrical portion; and
a second cylindrical portion disposed opposite the first cylindrical portion defining a radial gap therebetween;
wherein the first portion and the second portion to are further disposed to form an axial flow channel therebetween,
wherein the first and second portion overlap each other along an axial length;
wherein the axial flow channel provides a flow path for a drilling fluid from a top of the cylindrical portions to a bottom of the cylindrical portions; and
wherein the radial gap provides a flow path for the drilling fluid from the axial flow channel to a radial terminus of the first cylindrical portion and the second cylindrical portion.

2. The insert of claim 1, further comprising at least one end cap coupled to the first cylindrical portion and the second portion to prevent movement of the cylindrical portions when the insert is in use.

3. The insert of claim 1, wherein the first cylindrical portion and the second cylindrical portion are hemicylindrical defining two radial gaps from the axial flow channel to the radial terminus of the fracture insert.

4. The insert of claim 1, wherein the radial gap is parallel, nonparallel, straight, tortuous, or combinations thereof.

5. The insert of claim I, wherein the axial flow channel provides for flow substantially perpendicular to flow through the radial gap.

6. The insert of claim 1, wherein a width of the radial gap is within a range from about 0.1 mm to about 5 mm, and wherein an axial length of the radial gap is within a range from about 1 mm to about 150 mm.

7. A vessel comprising:
an inlet for receiving a drilling fluid;
a filtrate outlet; a fluid outlet; and
a fracture insert disposed within the vessel, wherein the insert comprises:
a first cylindrical portion opposite a second cylindrical portion defining a radial gap therebetween and further forming an axial flow channel therebetween;
wherein the first and second portion overlap each other along an axial length;
wherein the axial flow channel provides a flow path for the drilling fluid from the inlet to the fluid outlet; and
wherein the radial gap provides a flow path for the drilling fluid from the inlet to the filtrate outlet.

8. The vessel of claim 7, wherein the first cylindrical portion and the second cylindrical portion are hemicylindrical defining two radial gaps from the axial flow channel to a radial terminus of the insert.

9. The vessel of claim 7, wherein the radial gap is parallel, non-parallel, straight, tortuous, or combinations thereof.

10. The vessel of claim 7, wherein a width of the radial gap is within a range from about 0.1 mm to about 5 mm, and wherein an axial length of the radial gap is within a range from about 1 mm to about 150 mm.

11. A system comprising:
a vessel comprising:
an inlet for receiving a drilling fluid;
a filtrate outlet;
fluid outlet;
a fracture insert disposed within the vessel, wherein the insert comprises:
first cylindrical portion opposite a second cylindrical portion defining a radial gap therebetween and further forming an axial flow channel therebetween;
wherein the first and second portion overlap each other along an axial length;
wherein the axial flow channel provides a flow path from the inlet to the fluid outlet; and
wherein the radial gap provides a flow path from the inlet to the filtrate outlet;
a base fluid container in fluid communication with the inlet;
a test fluid container in fluid communication with the inlet;
a filtrate container in fluid communication with the filtrate outlet; and
a collection container in fluid communication with the fluid outlet.

12. The system of claim 11, wherein the radial gap is parallel, non-parallel, straight, tortuous, or combinations thereof.

13. The system of claim 11, wherein the first cylindrical portion and the second cylindrical portion are hemicylindrical defining two radial gaps from the axial flow channel to a radial terminus of the fracture insert.

14. The system of claim 11, wherein a width of the radial gap is within a range from about 0.1 mm to about 5 mm, and wherein an axial length of the radial gap is within a range from about 1mm to about 150 mm.

15. The system of claim 11 further comprising: a data acquisition system to receive data associated with the drilling fluid.

16. A method comprising:
injecting a first test fluid having a fluid loss control material to a vessel, the vessel comprising:
an inlet;
a filtrate outlet;
a fluid outlet; and
a fracture insert disposed within the vessel, wherein the fracture insert comprises:
a first cylindrical portion opposite a second cylindrical portion defining a radial gap therebetween and further forming an axial flow channel therebetween;
wherein the first and second portion overlap each other along an axial length;
wherein the axial flow channel provides a flow path from the inlet to the fluid outlet; and
wherein the radial gap provides a flow path from the inlet to the filtrate outlet; and
measuring a fluid loss through the radial gap.

17. The method of claim 16, further comprising:
stopping a flow of the first test fluid following at least a partial plugging of the radial gap with the fluid loss control material;

injecting a second test fluid to the vessel to simulate at least one of:
resuming drilling operations after the radial gap has been plugged;
continuing drilling operations during a fluid loss situation; and
breaking of a filter cake comprising the fluid loss control material using a breaker fluid.

18. The method of claim 16, further comprising:
removing at least one of the first cylindrical portion and the second cylindrical portion from the vessel;
inserting at least one of a third cylindrical portion and a fourth cylindrical portion into the vessel to define a second radial gap therebetween and forming a second axial flow channel; and
injecting the test fluid having the fluid loss control material from the test fluid container to the vessel; and
measuring a fluid loss through the second radial gap.

19. The method of claim 18, wherein the radial gap and the second radial gap have differences in at least one of a minimum gap width, a maximum gap width, an average gap width, and tortuosity.

20. The method of claim 16, further comprising determining a sealing parameter based on the fluid loss through the radial gap.

21. The method of claim 20, wherein the determining the sealing parameter comprises determining at least one of a seal location, particle size, reduction of fluid loss, and maximum sealing pressure.

22. A method for optimizing a drilling fluid, the method comprising:
injecting a drilling fluid having a first fluid loss control material particle size into a vessel, the vessel comprising:
an inlet;
a filtrate outlet;
a fluid outlet; and
a fracture insert disposed within the vessel, wherein the fracture insert comprises:
a first cylindrical portion opposite a second cylindrical portion defining a. radial gap therebetween and further forming an axial flow channel therebetween;
wherein the first and second portion overlap each other along an axial length;
wherein the axial flow channel provides a flow path from the fluid inlet to the fluid outlet; and
wherein the radial gap provides a flow path from the fluid inlet to the filtrate outlet; and
measuring a. fluid loss through the radial gap;
determining a sealing parameter based on the fluid loss; and
adjusting the fluid loss control material particle size based on the sealing parameter.

23. The method of claim 22, further comprising:
injecting the drilling fluid having the adjusted fluid loss control material particle size into the vessel; and
repeating the measuring, determining, adjusting, and injecting until the material particle size of the drilling fluid is optimized.

24. The method of claim 22, wherein the sealing parameter is at least one of a seal location, particle size, reduction of fluid loss, and maximum sealing pressure.

25. The method of claim 22, further comprising:
obtaining data from a remote data source for a current reservoir, the data including at least one of fracture width, fracture tortuosity, drilling fluid type, drilling fluid loss rates, and reservoir pressure; and
returning optimized drilling fluid parameters to the remote data source.

* * * * *